(12) United States Patent
Bozzano et al.

(10) Patent No.: US 7,732,650 B2
(45) Date of Patent: Jun. 8, 2010

(54) OXYGENATE CONVERSION TO OLEFINS WITH METATHESIS

(75) Inventors: Andrea G. Bozzano, Northbrook, IL (US); Bryan K. Glover, Algonquin, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 12/536,820

(22) Filed: Aug. 6, 2009

(65) Prior Publication Data

US 2009/0292151 A1  Nov. 26, 2009

Related U.S. Application Data

(62) Division of application No. 11/643,301, filed on Dec. 21, 2006, now abandoned.

(51) Int. Cl.
C07C 1/207 (2006.01)
C07C 6/04 (2006.01)

(52) U.S. Cl. .................. 585/317; 585/329; 585/638; 585/643

(58) Field of Classification Search .............. 585/317, 585/329, 638, 643
See application file for complete search history.

(56) References Cited

U.S. PATENT DOCUMENTS 5,990,369 A * 11/1999 Barger et al. ............... 585/640

* cited by examiner

*Primary Examiner*—Thuan Dinh Dang
(74) *Attorney, Agent, or Firm*—Arthur E Gooding

(57) ABSTRACT

A processing scheme and system for enhanced light olefin production, particularly for increased relative yield of propylene, involves oxygenate conversion to olefins and subsequent oxygenate conversion effluent stream treatment including cross-metathesis of 1-butene with 2-butene, metathesis of 2-butene with ethylene, conversion or removal of at least a portion of the isobutene, and/or isomerization of at least a portion of 1-butene to 2-butene to produce additional propylene. The processing scheme and system may further involve a reaction with distillation column for the metathesis of butenes with ethylene to produce propylene and/or a reaction with distillation column for the conversion of isobutenes with an oxygenate-containing material to produce a tertiary ether or alcohol.

6 Claims, 5 Drawing Sheets

OXYGENATE CONVERSION TO OLEFINS WITH METATHESIS

CROSS-REFERENCE TO RELATED APPLICATION

This application is a Division of copending U.S. application Ser. No. 11/643,301 filed Dec. 21, 2006, the contents of the contents of which are hereby incorporated by reference in its entirety.

FIELD OF THE INVENTION

This invention relates generally to the conversion of oxygenates to olefins and, more particularly, to light olefins.

BACKGROUND OF THE INVENTION

A major portion of the worldwide petrochemical industry is in involved with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the stream cracking of petroleum feeds. For various reasons including geographical, economic, political and diminished supply considerations, the art has long sought a source other than petroleum for the massive quantities of raw materials that are needed to supply the demand for these light olefin materials.

The search for alternative materials for light olefin production has led to the use of oxygenates such as alcohols and, more particularly, to the use of methanol, ethanol, and higher alcohols or their derivatives such as dimethyl ether, diethyl ether, etc., for example. Molecular sieves such as microporous crystalline zeolite and non-zeolite catalysts, particularly silicoaluminophosphates (SAPO), are known to promote the conversion of oxygenates to hydrocarbon mixtures, particularly hydrocarbon mixtures composed largely of light olefins.

Such processing of oxygenates to form light olefins is commonly referred to as a methanol-to-olefin (MTO) process, as methanol alone or together with other oxygenate materials such as dimethyl ether (DME) is typically an oxygenate material most commonly employed therein. In practice, such oxygenate conversion processing arrangements commonly produce ethylene and propylene as main products and, as stand alone processing, can achieve propylene to ethylene product ratios up to about 1.4. In addition to the production of ethylene and propylene as main products, such processing also typically produces or results in smaller relative amounts of highly olefinic $C_4$ and heavier hydrocarbon streams.

A process for the production of light olefins comprising olefins having from 2 to 4 carbon atoms per molecule from oxygenate feedstock generally typically involves passing the oxygenate feedstock to an oxygenate conversion zone containing a metal aluminophosphate catalyst to produce a light olefin stream. The light olefin stream is fractionated and a portion of the products are metathesized to enhance the yield of ethylene, propylene and/or butylene products. Propylene can be metathesized to produce more ethylene, or a combination of ethylene and butene can be metathesized to produce more propylene. The combination of light olefin production and metathesis or disproportionation is disclosed as providing flexibility such as to overcome the equilibrium limitations of the metal aluminophosphate catalyst in the oxygenate conversion zone. In addition, the invention thereof is disclosed as providing the advantage of extended catalyst life and greater catalyst stability in the oxygenate conversion zone.

While such processing can desirably result in the formation of increased relative amounts of propylene, further improvements such as to further enhance the relative amount of propylene production and recovery are desired and have been sought.

SUMMARY OF THE INVENTION

A general object of the invention is to provide or result in improved processing of an oxygenate-containing feedstock to light olefins.

A more specific objective of the invention is to overcome one or more of the problems described above.

The general object of the invention can be attained, at least in part, through a specified process for producing light olefins from an oxygenate-containing feedstock. In accordance with one embodiment, such a process involves contacting the oxygenate-containing feedstock in an oxygenate conversion reactor with an oxygenate conversion catalyst and at reaction conditions effective to convert the oxygenate-containing feedstock to form an oxygenate conversion effluent stream which includes light olefins and $C_4$+ hydrocarbons, wherein the light olefins comprises ethylene and the $C_4$+ hydrocarbons comprise a quantity of butenes including a quantity of 1-butenes and a quantity of isobutenes. The oxygenate conversion effluent stream is separated and forms a first process stream comprising at least a portion of the butenes, including at least a portion of the quantity of 1-butenes and at least a portion of the quantity of isobutenes, from the oxygenate conversion effluent stream. At least a portion of the quantity of butenes from the first process stream is contacted with a metathesis catalyst in a metathesis zone at effective conditions to produce a metathesis effluent stream comprising propylene. At least a portion of this propylene is desirably recovered from the metathesis effluent stream. In accordance with certain embodiments, the first process stream additionally comprises a quantity of 2-butenes which, upon contact with the metathesis catalyst, cross-metathesize with at least a portion of the 1-butenes from the first process stream to produce propylene.

The prior art generally fails to provide processing schemes and arrangements for the conversion of an oxygenate-containing feedstock to olefins that maximizes production of propylene to as great an extent as may be desired. Moreover, the prior art generally fails to provide a processing scheme and arrangement as effective and efficient as may be desired in increasing the relative yield of propylene in association with the conversion of oxygenate materials to light olefins.

A process for producing light olefins from an oxygenate-containing feedstock in accordance with another embodiment involves contacting the oxygenate-containing feedstock in an oxygenate conversion reactor with an oxygenate conversion catalyst and at reaction conditions effective to convert the oxygenate-containing feedstock to produce an oxygenate conversion effluent stream comprising light olefins and $C_4$+ hydrocarbons. The light olefins desirably include ethylene. The $C_4$+ hydrocarbons desirably include a quantity of butenes including a quantity of 1-butenes and a quantity of isobutenes. The oxygenate conversion effluent stream is treated to form a first process stream comprising at least a portion of the butenes including a portion of the quantity of 1-butenes and a portion of the quantity of isobutenes from the oxygenate conversion effluent stream. At least a portion of the quantity of isobutenes from the first process stream is converted in an isobutene conversion zone to form a second process stream including a quantity of 1-butenes and a third process stream including a conversion product. At least a portion of the quantity of 1-butenes from the second process stream is isomerized in an isomerization zone to produce an isomerized stream comprising a quantity of 2-butenes. At least a portion of the 2-butenes from the isomerized stream is contacted with ethylene in a metathesis zone at effective conditions to produce a metathesis effluent stream comprising propylene. Propylene is desirably recovered from the metathesis effluent stream.

There is also provided a system for producing light olefins from an oxygenate-containing feedstock. In accordance with one embodiment, such a system includes a reactor for contacting an oxygenate-containing feedstock with an oxygenate conversion catalyst and converting the oxygenate-containing feedstock to form an oxygenate conversion effluent stream comprising light olefins and $C_4+$ hydrocarbons, wherein the light olefins comprises ethylene and the $C_4+$ hydrocarbons comprise a quantity of butenes including a quantity of 1-butenes and a quantity of isobutenes. A separation zone is provided for separating the oxygenate conversion effluent stream and forming a first process stream comprising at least a portion of the quantity of butenes, including at least a portion of the quantity of 1-butenes and at least a portion of the quantity of isobutenes, from the oxygenate conversion effluent stream. A metathesis zone is provided for contacting at least a portion of the butenes from the first process stream with a metathesis catalyst to produce a metathesis effluent stream comprising propylene. The system further includes a recovery zone wherein in propylene is recovered from the metathesis effluent stream. In accordance with certain embodiments, the metathesis zone can comprise a reaction with distillation column containing a fixed bed of the metathesis catalyst wherein at least a portion of the quantity of butenes from the first process stream is contacted with ethylene to produce the metathesis effluent stream comprising propylene. The system can additionally include an isomerization zone, interposed between the separation zone and the metathesis zone, for isomerizing at least a portion of the quantity of 1-butenes from the first process stream to form an isomerized stream comprising a quantity of 2-butenes which can be subsequently metathesized in the metathesis zone to produce propylene. The system can also include an isobutene conversion zone wherein at least a portion of the quantity of isobutenes from the first process stream is converted to methyl tert-butyl ether.

As used herein, references to "light olefins" are to be understood to generally refer to $C_2$ and $C_3$ olefins, i.e., ethylene and propylene, alone or in combination.

References to "$C_x$ hydrocarbon" are to be understood to refer to hydrocarbon molecules having the number of carbon atoms represented by the subscript "x". Similarly, the term "$C_x$-containing stream" refers to a stream that contains $C_x$ hydrocarbon. The term "$C_x+$ hydrocarbons" refers to hydrocarbon molecules having the number of carbon atoms represented by the subscript "x" or greater. For example, "$C_4+$ hydrocarbons" include $C_4$, $C_5$ and higher carbon number hydrocarbons. The term "$C_x-$ hydrocarbons" refers to hydrocarbon molecules having the number of carbon atoms represented by the subscript "x" or fewer. For example, "$C_4-$ hydrocarbons" include $C_4$, $C_3$ and lower carbon number hydrocarbons.

Other objects and advantages will be apparent to those skilled in the art from the following detailed description taken in conjunction with the appended claims and drawings.

Those skilled in the art and guided by the teachings herein provided will recognize and appreciate that the illustrated systems or process flow diagrams have been simplified by the elimination of various usual or customary pieces of process equipment including some heat exchangers, process control systems, pumps, fractionation systems, and the like. It may also be discerned that the process flow diagrams depicted in the figures may be modified in many aspects without departing from the basic overall concept of the invention.

DETAILED DESCRIPTION

Oxygenate-containing feedstock can be converted to light olefins in a catalytic reaction. Heavier hydrocarbons (e.g., $C_4+$ hydrocarbons) formed during such processing can be subsequently treated such that at least a portion of a quantity of butenes formed upon such conversion are metathesized to produce additional propylene.

Figure 1:
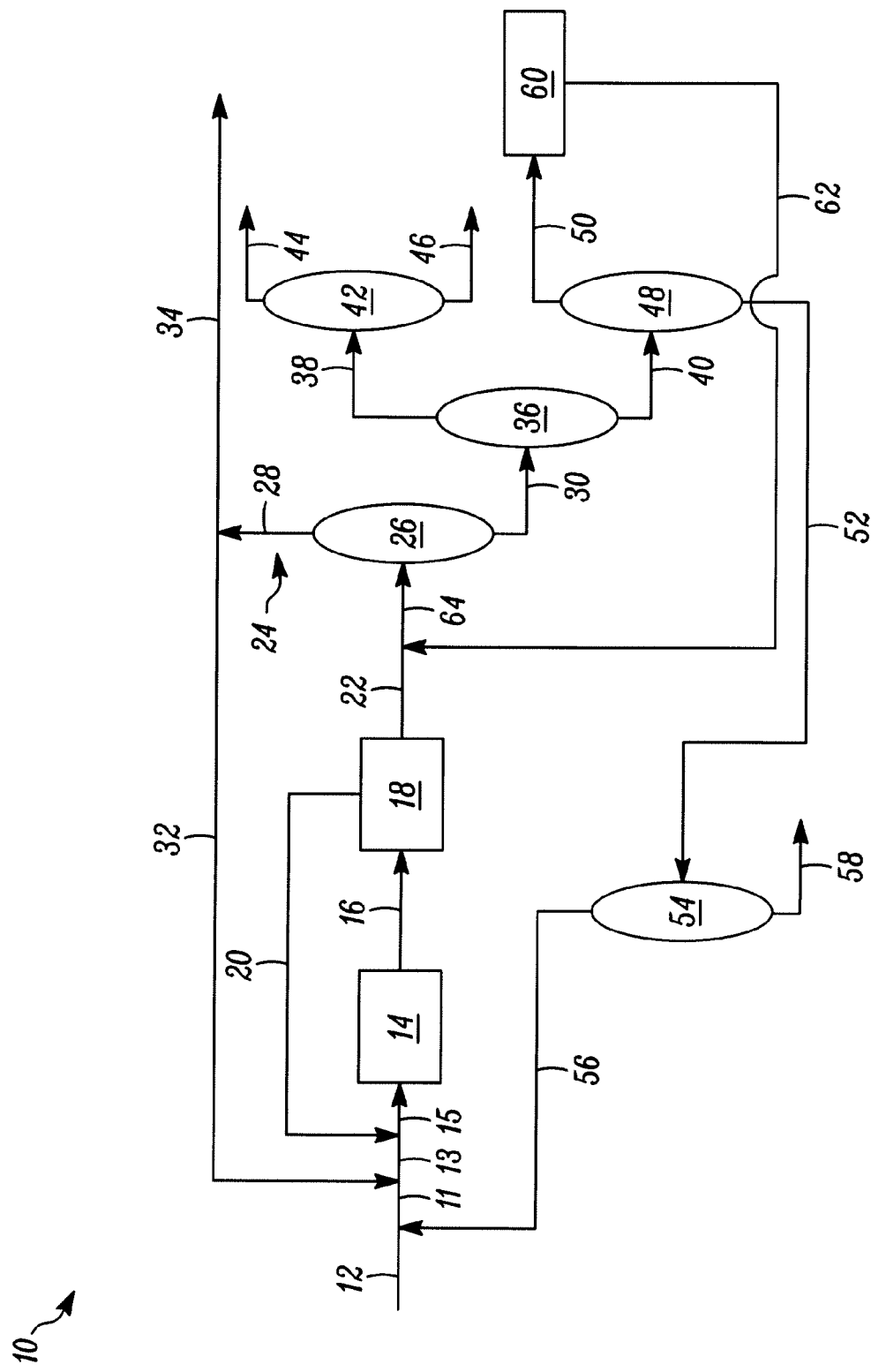
FIG. 1 is a simplified schematic process flow diagram illustrating a process for the conversion of oxygenates to olefins and employing a metathesis zone to enhance the yield of propylene in accordance with one embodiment.

As will be appreciated such processing may be embodied in a variety of processing arrangements. As representative, FIG. 1 illustrates a simplified schematic process flow diagram for a processing scheme, generally designated with the reference numeral 10, for the conversion of oxygenates to olefins and employing a metathesis zone to enhance the yield of propylene, in accordance with one embodiment.

More particularly, an oxygenate-containing feedstock or feedstream 12 such as generally composed of light oxygenates such as one or more of methanol, ethanol, dimethyl ether, diethyl ether, or combinations thereof, is introduced into an oxygenate conversion zone or reactor section 14 via lines 11, 13 and 15 wherein the oxygenate-containing feedstock 12 contacts an oxygenate conversion catalyst at reaction conditions effective to convert the oxygenate-containing feedstock to form an oxygenate conversion effluent stream comprising fuel gas hydrocarbons, light olefins, and $C_4+$ hydrocarbons, in a manner as is known in the art, such as, for example, utilizing a fixed, moving or fluidized bed reactor.

As will be appreciated by those skilled in the art and guided by the teachings herein provided, such a feedstock may be commercial grade methanol, crude methanol or any methanol purity therebetween. Crude methanol may be an unrefined product from a methanol synthesis unit. Those skilled in the art and guided by the teachings herein provided will understand and appreciate that in the interest of factors such as improved catalyst stability, embodiments utilizing higher purity methanol feed may be preferred. Thus, suitable feeds in such embodiments may comprise methanol or a methanol and water blend, with possible such feeds having a methanol content of between about 65% and about 100% by weight, preferably a methanol content of between about 80% and about 100% by weight and, in accordance with certain embodiments, a methanol content of between about 95% and about 100% by weight.

A methanol-to-olefin unit feedstream may comprise between about 0 wt. % and about 35 wt. % and more preferably about 5 wt. % and about 30 wt. % water. The methanol in the feedstream may comprise between about 70 wt. % and about 100 wt. % and more preferably between about 75 wt. % and about 95 wt. % of the feedstream. The ethanol in the feedstream may comprise between about 0.01 wt. % and about 0.5 wt. % and more typically between about 0.1 wt. % and about 0.2 wt. % of the feedstream although higher concentrations may be beneficial. When methanol is the primary component in the feedstream, the higher alcohols in the feedstream comprise between about 200 wppm and about 2000 wppm and more typically about between about 500 wppm and 1500 wppm. Additionally, when methanol is the primary component in the feedstream, dimethyl ether may comprise between about 100 wppm and about 20,000 wppm and more typically between about 200 wppm and about 10000 wppm.

The invention, however, also contemplates and encompasses embodiments wherein the oxygenate-containing feedstock includes dimethyl ether, either alone or in combination with water, methanol or in combination with both water and methanol, for example.

Reaction conditions for the conversion of oxygenate to light olefins are known to those skilled in the art. Preferably, in accordance with particular embodiments, reaction conditions comprise a temperature between about 200° C. and about 700° C., more preferably between about 300° C. and about 600° C., and most preferably between about 400° C. and about 550° C. In addition, reactor operating pressures typically are preferably superatmospheric and such as generally range from about 69 kPa to about 689 kPa (about 10 psig to about 100 psig), as may be required to accommodate sufficient pressure at the compressor section.

The oxygenate conversion reactor section 14 produces or results in formation of an oxygenate conversion reactor product or effluent stream 16 such as generally comprising fuel gas hydrocarbons, light olefins, and $C_4+$ hydrocarbons. The oxygenate conversion reactor effluent stream 16 is passed to an oxygenate treatment or recovery zone, generally designated by the reference numeral 18. The oxygenate recovery or treatment zone 18 generally typically includes one or more sections or units such as are known to those skilled in the art which can isolate, separate, remove and/or recycle various additional compounds or materials, such as, for example, excess oxygenate materials, water, oxygenate conversion catalyst fines and/or acid gases, from the oxygenate conversion reactor effluent stream 16. For example, as illustrated in FIG. 1, the oxygenate conversion reactor effluent stream 16 may be treated in the oxygenate recovery zone 18 to produce or result in the formation of an oxygenate recycle stream 20 and an oxygenate conversion effluent stream 22 which comprises a quantity of light olefins including ethylene and a quantity of $C_4+$ hydrocarbons including a quantity of butenes such as including a quantity of 1-butenes, a quantity of 2-butenes and a quantity of isobutenes. In accordance with certain embodiments, at least a portion of the oxygenate recycle stream 20 can be combined with at least a portion of the oxygenate-containing feedstock 12 and such combined stream can be introduced into the oxygenate conversion zone 14 via the line 15.

The oxygenate conversion effluent stream 22 can be further processed in a separation or treatment zone 24 wherein the oxygenate conversion effluent stream 22, or at least a portion thereof, may be separated or fractionated, such as by conventional distillation methods, to provide one or more process streams.

In accordance with certain embodiments, the oxygenate conversion effluent stream 22, or a select portion thereof, is passed to a deethanizer zone 26. In the deethanizer zone 26, the oxygenate conversion effluent stream 22 is fractionated, such as by conventional distillation methods, such as to provide or form a deethanizer overhead stream 28 comprising $C_2-$ hydrocarbons including methane, ethane, ethylene, and possibly also some inert species ($N_2$, CO, etc.), and a deethanized $C_3+$ bottoms stream 30 comprising components heavier than ethane, such as propylene, propane, mixed butenes and/or butane. The deethanizer overhead stream 28 or a portion thereof, such as, for example, a first portion 32, can be recycled to the oxygenate conversion zone 14. In practice, the first portion 32 of the deethanizer overhead stream 28 can be introduced directly into the oxygenate conversion zone 14. Alternatively, the first portion 32 of the deethanizer overhead stream can be combined with the oxygenate-containing feedstock 12 and/or the oxygenate recycle stream 20 and such combined stream can be introduced into the oxygenate conversion zone 14 via lines 13 and 15. Additionally or alternatively, the deethanizer overhead stream 28 or a portion thereof, such as, for example, a second portion 34, can be used as fuel.

The deethanized $C_3+$ bottoms stream 30, or at least a portion thereof, is passed to a depropanizer zone 36. In the depropanizer zone 36 the deethanized $C_3+$ bottoms stream 30 is treated or fractionated, such as by conventional distillation methods, to provide or form a depropanizer overhead stream 38 comprising $C_3$ materials and a depropanized stream 40 generally comprising $C_4+$ components. The depropanizer overhead stream 38, or at least a portion thereof, is passed to a $C_3$ splitter 42. In the $C_3$ splitter 42, the depropanizer overhead stream 38 is treated, e.g., fractionated, such as by conventional distillation methods, to provide an overhead propylene product stream 44 such as generally composed of propylene and a bottoms stream 46 such as generally composed of propane. The propane-containing bottoms stream 46 or a portion thereof can be recycled to a front-end synthesis gas unit or, if such unit is not readily available, can be used as fuel.

The depropanized stream 40, or at least a portion thereof, is passed to a $C_4$ fractionation zone 48. In the $C_4$ fractionation zone 48, the depropanized stream 40 is fractionated, such as by conventional distillation methods, to provide or form a mixed butenes stream 50 generally composed of 1-butenes, 2-butenes and isobutenes, and a $C_4$+stream 52 generally comprising $C_4$+ components other than butene.

In practice, such $C_4$+ stream 52 or a portion thereof can be passed to a heavy hydrocarbon separation zone 54. In the heavy hydrocarbon separation zone 54, the $C_4$+ stream 52 is fractionated, such as by conventional distillation methods, to provide or form an overhead stream 56 generally composed of $C_5$ and/or $C_6$ hydrocarbons and a bottoms stream 58 generally comprising components heavier than hexane. In practice, the overhead stream 56 or a portion there of can be directly recycled to the oxygenate conversion zone 14 for further processing. Alternatively, at least a portion of the overhead stream 56 can be combined with one or more of the oxygenate-containing feedstock 12, the oxygenate recycle stream 20, and the first portion 32 of the deethanizer overhead stream 28 and such combined stream can be introduced into the oxygenate conversion zone 14 via lines 11, 13 and 15. In practice, the bottoms stream 58 or a portion thereof can be used as fuel. For example, for locations in proximity to refineries, such materials or select portions thereof can be blended into a gasoline pool. Additionally or alternatively, depending upon the specifications as to the olefin content in a feed to a synthesis gas unit, the bottoms stream 58 or a portion thereof can be recycled to a front-end synthesis gas unit.

The mixed butenes stream 50, or at least a portion thereof, is introduced into a metathesis zone 60 and under effective conditions to produce a metathesis effluent stream 62 comprising propylene.

The metathesis reaction can generally be carried out under conditions and employs catalysts such as are known in the art. In accordance with one embodiment, a metathesis catalyst such as containing a catalytic amount of at least one of molybdenum oxide and tungsten oxide is suitable for the metathesis reaction. Conditions for the metathesis reaction generally include a reaction temperature ranging from about 20° C. to about 450° C., preferably 250° C. to 350° C., and pressures varying from about atmospheric to upwards of 20.6 MPa gauge (3000 psig), preferably between about 3000 kPa gauge to 3500 kPa gauge (435 psig to 510 psig), although higher pressures can be employed if desired. Catalysts which are active for the metathesis of olefins and which can be used in the process of this invention are of a generally known type. In this regard, reference is made to "Journal of Catalysis", 13 (1969) pages 99-114, to "Applied Catalysis", 10 (1984) pages 29-229 and to "Catalysis Review", 3 (1) (1969) pages 37-60. The disproportionation (metathesis) of 1-butene with 2-butene can, for example, be carried out in the liquid phase over a metathesis catalyst at about 20° C. to about 80° C. and at about 0.5 MPa to about 2 MPa (about 75 psi to about 290 psi).

Such metathesis catalysts may be homogeneous or heterogeneous, with the heterogeneous catalysts being preferred. The metathesis catalyst preferably comprises a catalytically effective amount of a transition metal component. The preferred transition metals for use in the present invention include tungsten, molybdenum, nickel, rhenium, and combinations thereof. The transition metal component may be present as elemental metal and/or one or more compounds of the metal. If the catalyst is heterogeneous, it is preferred that the transition metal component be associated with a support. Any suitable support material may be employed provided that it does not substantially interfere with the feedstock components or the lower olefin component conversion. Preferably, the support material is an oxide, such as silica, alumina, titania, zirconia, and combinations thereof. Silica is a particularly preferred support material. If a support material is employed, the amount of transition metal component used in combination with the support material may vary widely, depending, for example, on the particular application involved and/or the transition metal being used. Preferably, the transition metal comprises about 1% to about 20%, by weight (calculated as elemental metal) of the total catalyst. The metathesis catalyst advantageously comprise a catalytically effective amount of at least one of the above-noted transition metals, and are capable of promoting olefin metathesis. The catalyst may also contain at least one activating agent present in an amount to improve the effectiveness of the catalyst. Various activating agents may be employed, including activating agents which are well known in the art to facilitate metathesis reactions. Light olefins metathesis catalysts can, for example, desirably be complexes of tungsten (W), molybdenum (Mo), or rhenium (Re) in a heterogeneous or homogeneous phase.

In accordance with one embodiment, the metathesis reaction carried out within the metathesis zone 60 is a cross-metathesis reaction wherein 1-butenes from the mixed butenes stream 50 are reacted with 2-butenes from the mixed butenes stream 50 in the presence of a metathesis catalyst and at effective conditions to produce the metathesis effluent stream 62 predominantly composed of propylene and pentene. Generally, such cross-metathesis reaction is typically conducted in the absence of or without the presence of significant quantities of ethylene. In practice, pentenes from the metathesis effluent stream 62 can be recycled to the oxygenate conversion zone 14. Alternatively, in accordance with certain embodiments, the pentenes from the metathesis effluent stream 62 can be recycled to the separation zone 24.

Propylene is desirably recovered from the metathesis effluent stream 62. In accordance with one embodiment, propylene is recovered by introducing the metathesis effluent stream 62, or a select portion thereof, into the separation zone 24. For example, the metathesis effluent stream 62, or at least a portion thereof, can be combined with the oxygenate conversion effluent stream 22 and such combined stream can be introduced into the separation section 14 via a line 64 wherein propylene is recovered from such combined stream according to the processes described above in conjunction with the deethanizer zone 26, the depropanizer zone 36 and the $C_3$ splitter 42.

Alternatively, the metathesis effluent stream 62, or at least a portion thereof, can be passed to a metathesis fractionation zone (not shown) wherein the metathesis effluent stream 62 is resolved, e.g., fractionated, by conventional separation means into a product propylene stream and a higher hydrocarbon fraction including butene which can be recycled back into the processing scheme such as, for example, back into the any one of the deethanizer zone 26, the depropanizer zone 36, the $C_4$ fractionation zone 48, or the metathesis zone 60. In embodiments wherein such higher hydrocarbon fraction from the metathesis fractionation zone is recycled to the metathesis zone 60, a drag stream may be provided to reduce the build-up of higher hydrocarbon components such as, for example, isobutene.

In accordance with certain embodiments, and as described in further detail below in conjunction with FIG. 3, the mixed butenes stream 50, or at least a portion thereof, can be treated in an isobutene conversion zone to remove at least a portion of the quantity of isobutenes from the mixed butenes stream 50 prior to contacting the metathesis catalysts in the metathesis zone 60. Removal of such isobutenes fraction from the mixed butenes stream 50 prior to metathesis is generally, typically found to result in improved propylene yields.

Figure 2:
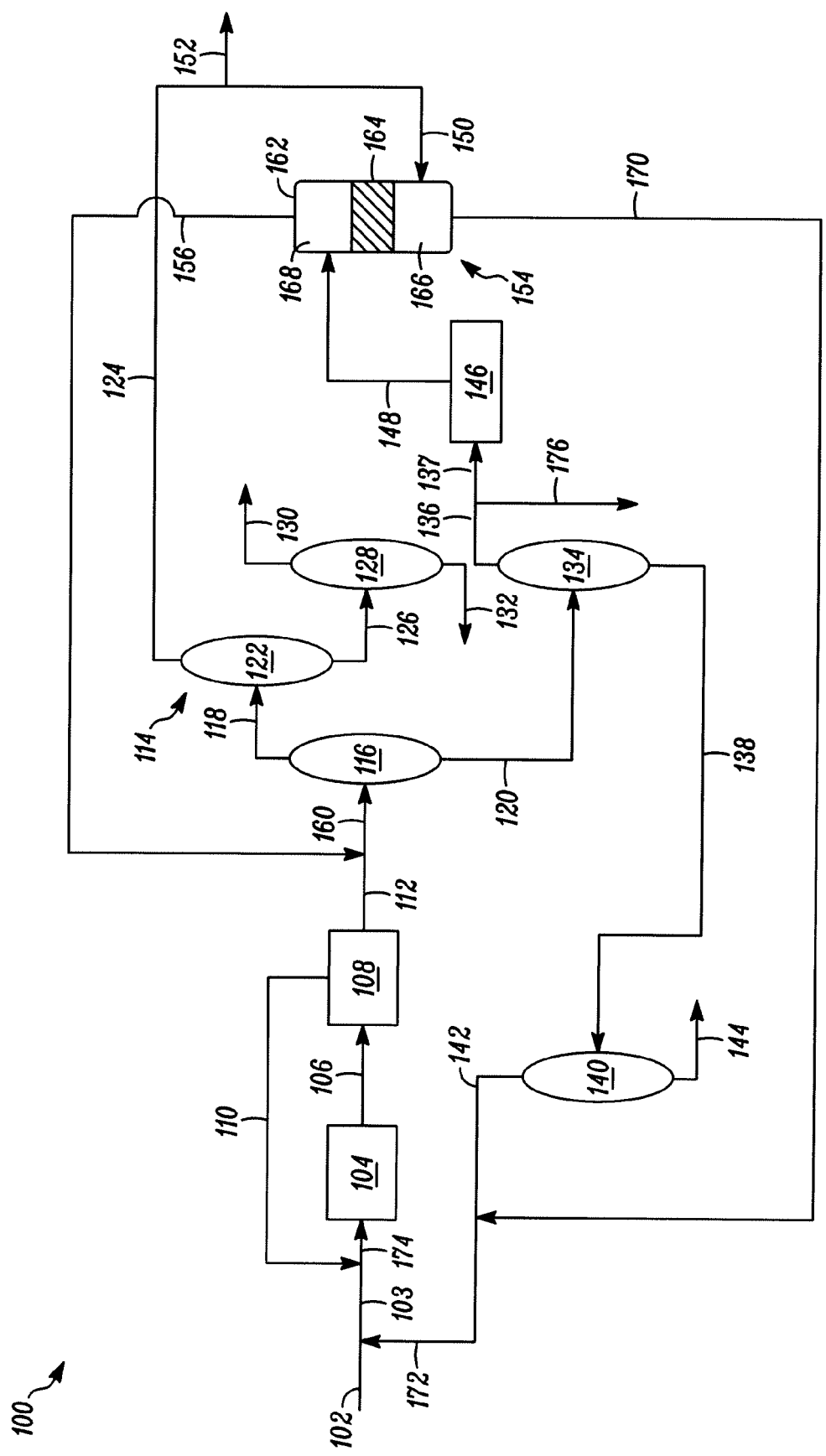
FIG. 2 is a simplified schematic process flow diagram illustrating a process for the conversion of oxygenates to olefins employing a metathesis zone including a reaction with distillation column, to enhance the yield of propylene, in accordance with an additional embodiment.

In accordance with another embodiment, as illustrated in FIG. 2, a processing scheme 100 for producing light olefins from an oxygenate-containing feedstock involves introducing an oxygenate-containing feedstock or feedstream 102 such as generally composed of light oxygenates such as one or more of methanol, ethanol, dimethyl ether, diethyl ether, or combinations thereof, is introduced via lines 103 and 174 into an oxygenate conversion zone or reactor section 104 wherein the oxygenate-containing feedstock contacts an oxygenate conversion catalyst at reaction conditions effective to convert the oxygenate-containing feedstock to form an oxygenate conversion reactor effluent stream 106 comprising fuel gas hydrocarbons, light olefins, and $C_4+$ hydrocarbons.

The oxygenate conversion reactor effluent stream 106, or at least a portion thereof, is passed to an oxygenate treatment or recovery zone, generally designated by the reference numeral 108. The oxygenate conversion reactor effluent stream 106 is treated in the oxygenate recovery zone 108 to produce or result in the formation of an oxygenate recycle stream 110 and an oxygenate conversion effluent stream 112 which comprises a quantity of light olefins including ethylene and a quantity of $C_4+$ hydrocarbons including a quantity of butenes such as including a quantity of 1-butenes, a quantity of 2-butenes and a quantity of isobutenes.

In practice, the oxygenate recycle stream 110, or at least a portion thereof, can be introduced directly into the oxygenate conversion zone 104 for further processing. Alternatively, the oxygenate recycle stream 110 may be combined with the oxygenate feedstock 102 and introduced into the oxygenate conversion zone 104 via a line 174.

The oxygenate conversion effluent stream 112, or at least a portion thereof, may be further processed in a separation or treatment zone 114 wherein the oxygenate conversion effluent stream 112 may be separated or fractionated such as by conventional distillation methods, to provide one or more process streams.

In accordance with certain embodiments, the oxygenate conversion effluent stream 112, or at least a portion thereof, is passed to a depropanizer zone 116. In the depropanizer zone 116, the oxygenate conversion effluent stream 112 is fractionated, such as by conventional distillation methods, such as to provide or form a depropanizer overhead stream 118 comprising $C_3-$ hydrocarbons including methane, ethane, ethylene, propane, propylene and possibly also some inert species ($N_2$, CO, etc.), and a depropanized $C_4+$ bottoms stream 120 comprising components heavier than propane, such as mixed butenes and/or butane.

The depropanizer $C_3-$ overhead stream 118, or at least a portion thereof, is passed to a deethanizer zone 122. In the deethanizer zone 122 the depropanizer $C_3-$ overhead stream 118 is treated or fractionated, such as by conventional distillation methods, to provide or form a deethanizer overhead stream 124 comprising $C_2-$ materials including ethylene and a deethanized stream 126 generally comprising $C_3$ materials including propane and propylene. The deethanized stream 126, or at least a portion thereof, is passed to a $C_3$ splitter 128. In the $C_3$ splitter 128, the deethanized stream 126 is treated, e.g., fractionated, such as by conventional distillation methods, to provide an overhead propylene product stream 130 such as generally composed of propylene and a bottoms stream 132 such as generally composed of propane. The propane-containing bottoms stream 132, or a portion thereof, can be recycled to a front-end synthesis gas unit or, if such unit is not readily available, can be used as fuel.

The depropanized stream 120, or at least a portion thereof, is passed to a $C_4$ fractionation zone 134. In the $C_4$ fractionation zone 134, the depropanized stream 120 is fractionated, such as by conventional distillation methods, to provide or form a mixed butenes stream 136 generally composed of 1-butenes, 2-butenes and isobutenes, and a $C_4+$ stream 138 generally comprising $C_4+$ components other than butene.

In practice, the $C_4+$ stream 138 or a portion thereof can be passed to a heavy hydrocarbon separation zone 140. In the heavy hydrocarbon separation zone 140, the $C_4+$ stream 138 is fractionated, such as by conventional distillation methods, to provide or form an overhead stream 142 generally composed of $C_5$ and/or $C_6$ hydrocarbons and a bottoms stream 144 generally comprising components heavier than hexane. In practice the overhead stream 142 or a portion there of can be recycled to the oxygenate conversion zone 104 such as, for example, via lines 172, 103 and 174, for further processing. In practice, the bottoms stream 144 or a portion thereof can be used as fuel. For example, for locations in proximity to refineries, such materials or select portions thereof can be blended into a gasoline pool. Additionally or alternatively, depending upon the specifications as to the olefin content in a feed to a synthesis gas unit, the bottoms stream 144 or a portion thereof can be recycled to a front-end synthesis gas unit.

It has been found that the metathesis reaction of butenes with ethylene over a metathesis catalyst to produce propylene is favored where the butenes are in the form of 2-butenes rather than 1-butenes. Thus, in accordance with one embodiment, and as described in greater detail below, the mixed butenes stream 136, or at least a portion thereof, is passed via the line 137 to an isomerization zone 146 for isomerizing at least a portion of the quantity of 1-butenes therein contained to form an isomerized stream 148 comprising an increased quantity of 2-butenes.

As will be appreciated, such isomerization of 1-butenes to 2-butenes can desirably occur over a suitable isomerization catalyst at selected appropriate isomerization reaction conditions. The 1-butene to 2-butene isomerization reaction is actually a hydroisomerization as it is generally conducted in the presence of a hydrogen atmosphere to facilitate the double bond migration, but such that the use of hydrogen is minimized to avoid undesirable hydrogenation side reactions. The catalysts typically employed in such processing are commonly based on noble metals (palladium, rhodium, platinum, etc.) deposited on an inert alumina support; palladium is normally preferred. Typical or usual reaction conditions may involve a temperature of about 100° C. to about 150° C. and typically a pressure of about 1.5 MPa to 2 MPa (about 215 psia to 300 psia). The feed to the hydroisomerization reactor is usually preheated by exchange with the reactor effluent and by steam. Such a heated feed then enters the reactor, which typically operates in a mixed phase with one or more catalyst beds. After cooling the isomerization products are typically flashed to remove excess hydrogen gas. The reaction temperature is generally chosen so as to maximize conversion to 2-butene (favored by lower temperatures) while still having a reasonable rate of reaction; hence it is commonly desirable to operate at a temperature of less than 150° C. Desirably, the isomerized stream will contain 2-butene and 1-butene in a molar ratio of at least 8, e.g., at least 8 moles of 2-butenes per mole of 1-butenes, and, in accordance with at least certain embodiments, a molar ratio of greater than 10, e.g., more than 10 moles of 2-butene per mole of 1-butene. If fractionated, the residual 1-butene can be recycled to the isomerization reactor.

At least a portion of the isomerized stream 148 and a quantity of ethylene, such as a portion of the above-described deethanizer overhead stream 124 via a line 150, are introduced into a metathesis zone 154 to produce a metathesis effluent stream 156 comprising propylene. In accordance with certain embodiments, a drag or purge line 152 drawn off line 150 can be provided to avoid undesired build-up of carbon dioxide (CO) or other nonreacting materials (e.g., ethane) that might otherwise accumulate in the process loop. Alternatively or additionally, a demethanizer zone can be disposed between the deethanizer zone 122 and the metathesis zone 154 to treat, e.g., fractionate, the deethanizer overhead stream 124 to provide a demethanized stream comprising ethylene which can be introduced into the metathesis zone 154 via the line 150. Such treatment of the deethanizer overhead stream 124 in the demethanizer zone can generally typically be employed to avoid the undesired build-up of carbon dioxide in the metathesis zone 154 and to prolong the life of the metathesis catalyst.

The metathesis reaction can generally employ catalysts such as described in detail above in conjunction with the metathesis zone 60 as illustrated in FIG. 1. Generally, the disproportionation (metathesis) of 2-butene with ethylene can, for example, be carried out in the vapor phase at about 300° C. to about 350° C. and about 0.5 MPa absolute (75 psia) with a WHSV of 50 to 100 and a once-through conversion of about 15%, depending on the ethylene to 2-butene ratio.

Propylene is desirably recovered from the metathesis effluent stream 156. In accordance with one embodiment, at least a portion of the metathesis effluent stream 156 can be recycled into the separation or treatment zone 114. For example, at least a portion of the metathesis effluent stream 156 can be combined with at least a portion of the oxygenate conversion effluent stream 112 and a combined stream 160 can be introduced into the separation zone 114 wherein propylene can be recovered from the combined stream 160 according to the process described above in conjunction with operation of the depropanizer zone 116, the deethanizer zone 122 and the $C_3$ splitter 128.

In accordance with certain embodiments, the metathesis zone 154 can comprise a reaction with distillation column 162 containing a fixed bed 164 of the metathesis catalyst. The reaction with distillation column 162 generally includes a stripping section 166, disposed below the fixed catalyst bed 164, containing a distillation structure such as, for example, trays or inert packing as is known in the art and a distillation section 168, disposed above the fixed catalyst bed 164, containing a distillation structure as is known in the art.

Suitable metathesis catalysts for use in the fixed bed 164 generally, typically include supported oxides of cobalt, molybdenum, rhenium or mixtures of cobalt and molybdenum oxides. Suitable supports for the oxides include, for example, silica and alumina. Typically, the reaction with distillation column is operated at a pressure effective to result in a fixed catalyst bed temperature of about 100° C. to about 200° C.

In practice, 2-butenes from the isomerized stream 148 are introduced into the reaction with distillation column 162 above the fixed catalyst bed 164 and ethylene, via the line 150, is introduced below the fixed catalyst bed 164. The ethylene flows upward into the fixed bed 164 and reacts with 2-butene to produce propylene which is removed via the overhead metathesis effluent stream 156. The distillation section 168 above the fixed bed 164 separates unreacted 2-butene from propylene and recycles the 2-butene to fixed catalyst bed 164. Generally, 2-butene is present in an excess relative to ethylene, e.g., a ratio of about 25:1 2-butene to ethylene. A metathesis bottoms stream 170 is provided to remove any heavier components, i.e., components heavier than pentane, produced during the metathesis reaction from the reaction with distillation column 162.

In accordance with certain embodiments, at least a portion of the metathesis bottoms stream 170 can be recycled to the oxygenate conversion zone 104 for further processing. For example, at least a portion of the metathesis bottoms stream 170 can be combined with at least a portion of the overhead stream 142 and such combined stream can be fed directly to the oxygenate conversion zone 104. Alternatively, the combined stream can be combined with the oxygenate feedstock 102 and introduced into the oxygenate conversion zone 104 via lines 172, 103 and 174. Alternatively, in accordance with certain other embodiments, the metathesis bottoms stream 170, or at least a portion thereof, can be recycled to the isomerization zone 146.

In accordance with another embodiment, the processing scheme 100 may further include an isobutene conversion zone disposed between the $C_4$ fractionation zone 134 and the isomerization zone 146. As discussed in greater detail below, and in conjunction with FIG. 3, at least a portion of the mixed butenes stream 136 may be treated in the isobutene conversion zone to remove at least a portion of the quantity of isobutenes from the mixed butenes stream 146 prior to isomerization of at least a portion of the 1-butenes in the isomerization zone 146.

In accordance with certain other embodiments, the processing scheme can further include a $C_4$ purge stream 176 to avoid undesired build-up of heavy hydrocarbons or other nonreacting materials (e.g., saturates) and, particularly, isobutenes that might otherwise accumulate in the process loop. The $C_4$ purge stream 176 can be disposed between the $C_4$ fractionation section 134 and the isomerization section 146, i.e., drawn off from the mixed butenes stream 136, as illustrated in FIG. 2. Alternatively, the $C_4$ purge stream 176 may be disposed between the isomerization zone 146 and the metathesis zone 154, i.e., drawn off from the isomerized stream 148. Alternatively or additionally, a purge stream can be drawn off the metathesis bottoms stream 170.

Figure 3:
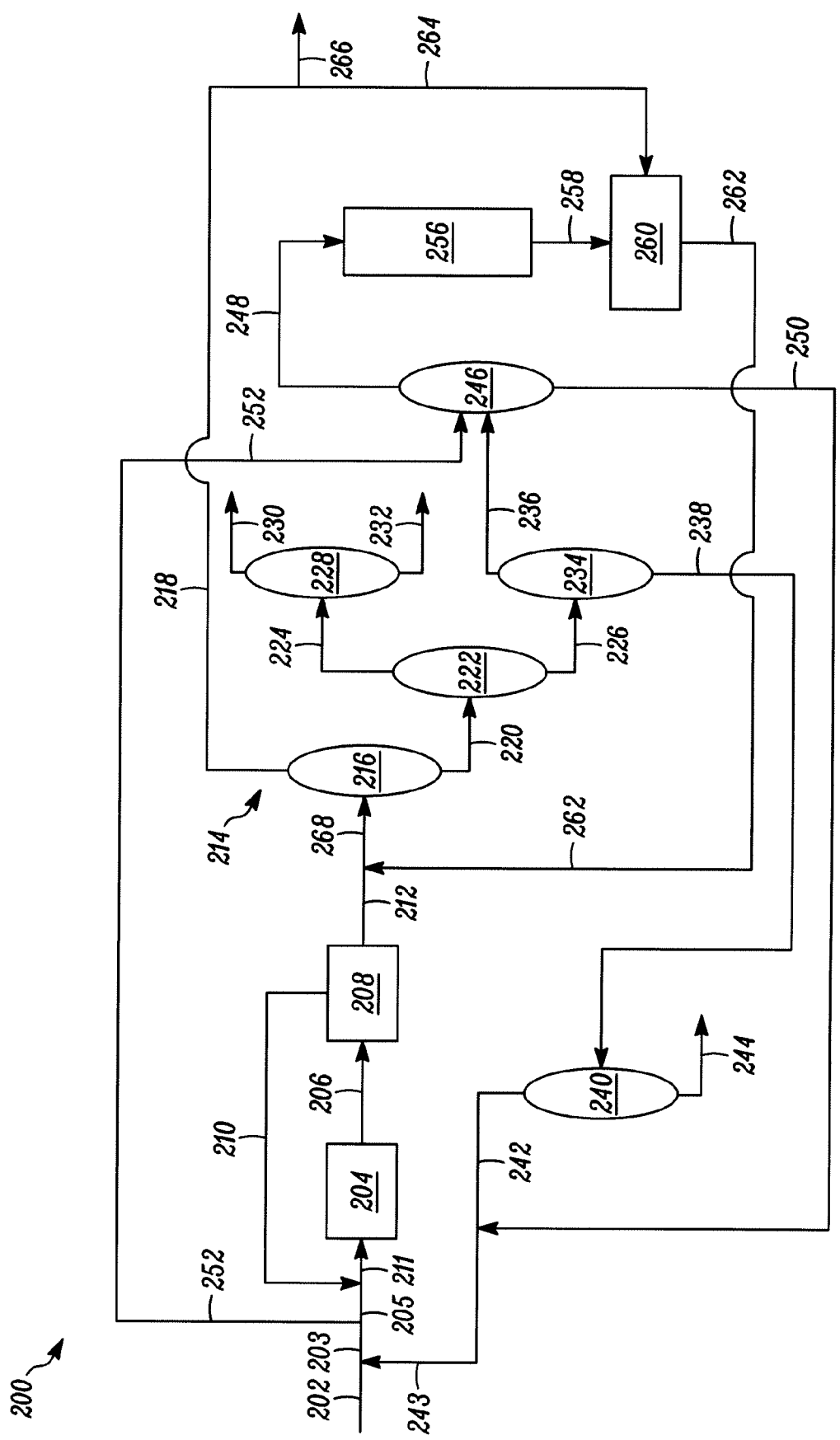
FIG. 3 is a simplified schematic process flow diagram illustrating a process for the conversion of oxygenates to olefins and employing a separation zone, to form a butene-containing stream, an isobutene conversion zone, to reduce the relative amount of isobutenes, an isomerization zone, to enhance the relative amount of 2-butene, and a metathesis zone, to enhance the yield of propylene, in accordance with another embodiment.

In accordance with a further embodiment, as illustrated in FIG. 3, a processing scheme 200 for producing light olefins from an oxygenate-containing feedstock involves introducing an oxygenate-containing feedstock or feedstream 202 such as generally composed of light oxygenates such as one or more of methanol, ethanol, dimethyl ether, diethyl ether, or combinations thereof, is introduced via lines 203, 205 and 211 into an oxygenate conversion zone or reactor section 204 wherein the oxygenate-containing feedstock contacts an oxygenate conversion catalyst at reaction conditions effective to convert the oxygenate-containing feedstock to form an oxygenate conversion reactor effluent stream 206 comprising fuel gas hydrocarbons, light olefins, and $C_4+$ hydrocarbons. In accordance with certain embodiments, the oxygenate-containing feedstock 202 desirably comprises methanol.

The oxygenate conversion reactor effluent stream 206, or at least a portion thereof, is passed to an oxygenate treatment or recovery zone, generally designated by the reference numeral 208. The oxygenate conversion reactor effluent stream 206 is treated in the oxygenate recovery zone 208 to produce or result in the formation of an oxygenate recycle stream 210 and an oxygenate conversion effluent stream 212 which comprises a quantity of light olefins including ethylene and a quantity of $C_4+$ hydrocarbons including a quantity of butenes such as including a quantity of 1-butenes, a quantity of 2-butenes and a quantity of isobutenes.

In practice, the oxygenate recycle stream 210 can be introduced directly into the oxygenate conversion zone 204 for further processing. Alternatively, the oxygenate recycle stream 210 may be combined with the oxygenate feedstock 202 and introduced into the oxygenate conversion zone 204 via the line 211. In accordance with certain embodiments, the oxygenate recycle stream 210 desirably comprises a quantity of methanol.

The oxygenate conversion effluent stream 212 can be further processed in a separation or treatment zone 214 wherein at least a portion of the oxygenate conversion effluent stream 212 is passed via a line 268 to a deethanizer zone 216. In the deethanizer zone 216, the oxygenate conversion effluent stream 212 is fractionated, such as by conventional distillation methods, such as to provide or form a deethanizer overhead stream 218 comprising $C_2-$ hydrocarbons including methane, ethane, ethylene, and possibly also some inert species ($N_2$, CO, etc.), and a deethanized $C_3+$ bottoms stream 220 comprising components heavier than ethane, such as propylene, propane, mixed butenes and/or butane.

The deethanized $C_3+$ bottoms stream 220, or at least a portion thereof, is passed to a depropanizer zone 222. In the depropanizer zone 222 the deethanized $C_3+$ bottoms stream 220 is treated or fractionated, such as by conventional distillation methods, to provide or form a depropanizer overhead stream 224 comprising $C_3$ materials and a depropanized stream 226 generally comprising $C_4+$ components. The depropanizer overhead stream 224 is passed to a $C_3$ splitter 228. In the $C_3$ splitter 228, the depropanizer overhead stream 224, or at least a portion thereof, is treated, e.g., fractionated, such as by conventional distillation methods, to provide an overhead propylene product stream 230 such as generally composed of propylene and a bottoms stream 232 such as generally composed of propane. The propane-containing bottoms stream 232, or a portion thereof, can be recycled to a front-end synthesis gas unit or, if such unit is not readily available, can be used as fuel.

The depropanized stream 226, or at least a portion thereof, is passed to a $C_4$ fractionation zone 234. In the $C_4$ fractionation zone 234, the depropanized stream 226 is fractionated, such as by conventional distillation methods, to provide or form a mixed butenes stream 236 generally composed of 1-butenes, 2-butenes and isobutenes, and a $C_4+$ stream 238 generally comprising $C_4+$ components other than butene.

In practice, the $C_4+$ stream 238, or at least a portion thereof, can be passed to a heavy hydrocarbon separation zone 240. In the heavy hydrocarbon separation zone 240, the $C_4+$ stream 238 is fractionated, such as by conventional distillation methods, to provide or form an overhead stream 242 generally composed of $C_5$ and/or $C_6$ hydrocarbons and a bottoms stream 244 generally comprising components heavier than hexane. In practice, the overhead stream 242, or a portion thereof, can be recycled to the oxygenate conversion zone 204 such as, for example, via lines 243, 203, 205 and 211, for further processing. In practice, the bottoms stream 244, or at least a portion thereof, can be used as fuel. For example, for locations in proximity to refineries, such materials or select portions thereof can be blended into a gasoline pool. Additionally or alternatively, depending upon the specifications as to the olefin content in a feed to a synthesis gas unit, the bottoms stream 244 or a portion thereof can be recycled to a front-end synthesis gas unit.

It has been found that reduction or removal of at least a portion of the quantity of isobutenes from the mixed butenes stream 236 can beneficially improve the yield of propylene from the process. Accordingly, in one embodiment, at least a portion of the mixed butenes stream 236 is passed to an isobutene conversion zone 246 wherein at least a portion of the quantity of isobutenes from the mixed butenes stream 236 is converted to produce a conversion product at least a portion of which can be removed from and/or recycled into the process 200.

For example, at least a portion of the quantity of isobutenes from the mixed butenes stream 236 can be converted by reacting the isobutenes with an oxygenate-containing material such as, for example, methanol, ethanol or a combination thereof, to produce a second process stream 248 including a quantity of 1-butenes and a third process stream 250 including a tertiary ether or alcohol product. In accordance with certain embodiments, at least a portion of the mixed butenes stream 236 including a quantity of isobutenes is combined with a methanol-containing material in the presence of an acid catalyst to produce the third process steam 250 including methyl tert-butyl ether. In accordance with certain other embodiments, at least a portion of the third process stream 250 can form a methyl tert-butyl ether product stream wherein such methyl tert-butyl ether can be utilized as a gasoline additive.

In accordance with one embodiment, a portion of the oxygenate-containing feedstock 202 can be passed via a line 252 to the isobutene conversion 246 to react with at least a portion of the quantity isobutenes from the mixed butenes stream 236. At least a portion of the third process stream 250 can be recycled to the oxygenate conversion zone 204 to produce an additional quantity of light olefins. For example, at least a portion of the third process stream 250 can be introduced directly into the oxygenate conversion zone 204. Alternatively, at least a portion of the third process stream 250 can be combined with the oxygenate-containing feedstock 202 and/or the overhead stream 242 and introduced into the oxygenate conversion zone 204 via the lines 243, 203, 205 and 211.

In accordance with another embodiment, the isobutene conversion zone 246 may desirably incorporate both a reaction step and a fractionation step. For example, the isobutene conversion zone 246 can include a reaction with distillation column) wherein at least a portion of the quantity of isobutenes from the mixed butenes stream 236 are reacted with an oxygenate-containing material such as methanol and the resulting reaction products are fractionated to form the second process stream 248 and the third process stream 250.

In accordance with a further embodiment, at least a portion of the quantity of isobutenes from the mixed butenes stream 236 can be converted by dimerizing the isobutenes with 1-butenes and/or 2-butenes from the mixed butenes stream 236 over an acid catalyst to produce a dimerization effluent stream comprising 1-butenes, 2-butenes, a reduced quantity of isobutenes, and a conversion product such as comprising $C_8$ and/or $C_{12}$ hydrocarbons. The dimerization effluent stream can be resolved, i.e., fractionated, by conventional distillation means to produce the second process stream 248 and the third process stream 250 comprising the conversion product.

The dimerization reaction can generally be carried out in a dimerization unit or reactor including one or more fixed beds containing an acid catalyst and at conditions effective to react no more than two moles of normal butenes (i.e., mixed 1-butenes and 2-butenes) per mole of isobutene and, suitably, less than one mole of normal butenes per mole of isobutenes. Conditions for the dimerization reaction using solid phosphoric acid (SPA) catalyst generally include a reaction temperature ranging from about 120° C. to about 260° C., and pressures varying from about 103.4 kPa to about 8.3 MPa (about 15 psig to about 1200 psig), typically from about 2.8 MPa to about 6.9 MPa (about 400 psig to about 1000 psig). Other dimerization catalysts which can generally be employed in the fixed beds include acidic resin catalysts such as, for example, Amberlist 15 and/or Amberlist 35.

In accordance with one embodiment, the second process stream 248, or at least a portion thereof, can be passed to an isomerization zone 256 for isomerizing at least a portion of the quantity of 1-butenes from the second process stream 248 to form an isomerized stream 258 comprising an increased quantity of 2-butenes. The isomerization zone 256 may be configured and/or operated in a manner such as described above in conjunction with isomerization zone 146, illustrated in FIG. 2.

Alternatively, a dimerization reaction employing a SPA catalyst can generally be carried out in the isobutene conversion zone 246 at conditions effective to additionally convert 1-butenes from the mixed butenes stream 236 to 2-butenes to form a process stream including an additional quantity of 2-butenes. Such process stream can be introduced directly into a metathesis zone wherein the 2-butenes are contacted with ethylene over a metathesis catalyst to produce propylene.

At least a portion of the 2-butenes from the isomerized stream 258 and a quantity of ethylene, such as a portion of the above-described deethanizer overhead stream 218 via a line 264, are introduced into a metathesis zone 260 to produce a metathesis effluent stream 262 comprising propylene. In accordance with certain embodiments, a drag or purge line 266 can be drawn off line 218 to avoid undesired build-up of carbon dioxide (CO) or other nonreacting materials (e.g., ethane) that might otherwise accumulate in the process loop. In accordance with certain other embodiments, and as described in greater detail below in conjunction with FIG. 4, the deethanizer overhead stream 218 can be fractionated, such as by conventional distillation methods, to produce an ethylene-containing stream which can be introduced into the metathesis zone 260.

The metathesis zone 260 can employ or contain a catalyst such as, for example, described above in conjunction with the metathesis zone 60, illustrated in FIG. 1. The metathesis of 2-butene with ethylene can, for example, be carried out in the vapor phase at about 300° C. to about 350° C. and about 0.5 MPa (75 psia) with a WHSV of 50 to 100 and a once-through conversion of about 15%, depending on the ethylene to 2-butene ratio. In accordance with certain embodiments, the metathesis zone 260 can include a reaction with distillation column as described above in conjunction with metathesis zone 154, illustrated in FIG. 2.

In accordance with one embodiment, at least a portion of the metathesis effluent stream 262 can be recycled into the separation or treatment zone 214. For example, at least a portion of the metathesis effluent stream 262 can be combined with at least a portion of the oxygenate conversion effluent stream 212 and such combined stream can be introduced via the line 268 into the separation zone 214 wherein propylene can be recovered from the combined stream according to the process described above in conjunction with the depropanizer zone 216, the deethanizer zone 222 and the $C_3$ splitter 228.

Figure 4:
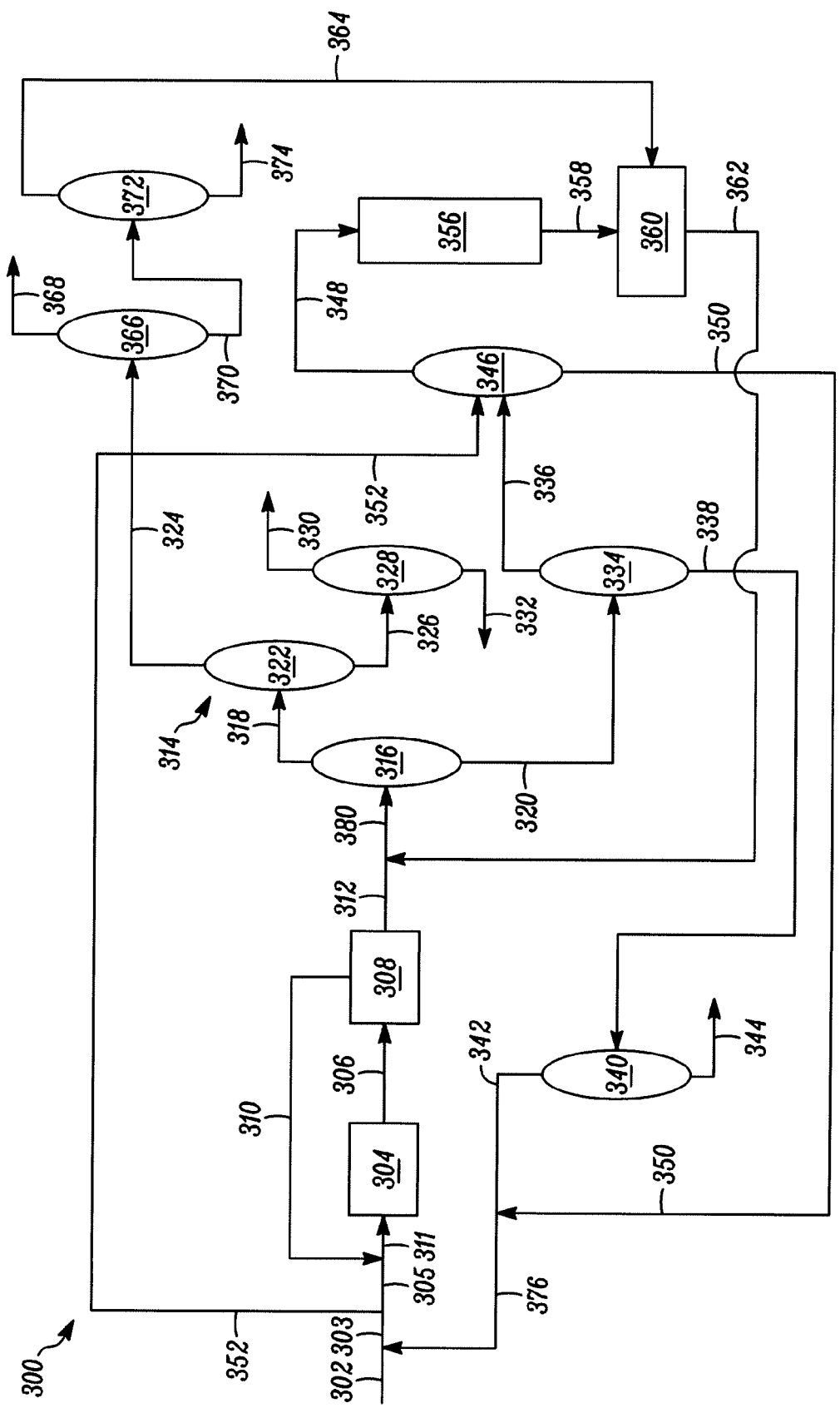
FIG. 4 is a simplified schematic process flow diagram illustrating a process for the conversion of oxygenates to olefins and employing a separation zone, to form a butene-containing stream, an isobutene conversion zone, to reduce the relative amount of isobutenes, an isomerization zone, to enhance the relative amount of 2-butene, and a metathesis zone, to enhance the yield of propylene, in accordance with a further embodiment.

In accordance with an additional embodiment, as illustrated in FIG. 4, a processing scheme 300 for producing light olefins from an oxygenate-containing feedstock involves introducing an oxygenate-containing feedstock or feedstream 302, such as generally composed of methanol, is introduced via lines 303, 305 and 311 into an oxygenate conversion zone or reactor section 304 wherein the oxygenate-containing feedstock 302 contacts an oxygenate conversion catalyst at reaction conditions effective to convert the oxygenate-containing feedstock to form an oxygenate conversion reactor effluent stream 306 comprising fuel gas hydrocarbons, light olefins, and $C_4$+ hydrocarbons.

At least a portion of the oxygenate conversion reactor effluent stream 306 is passed to an oxygenate treatment or recovery zone, generally designated by the reference numeral 308. The oxygenate conversion reactor effluent stream 306 is treated in the oxygenate recovery zone 308 to produce or result in the formation of an oxygenate recycle stream 310, such as generally composed of methanol, and an oxygenate conversion effluent stream 312 which comprises a quantity of light olefins including ethylene and a quantity of $C_4$+ hydrocarbons including a quantity of butenes such as including a quantity of 1-butenes, a quantity of 2-butenes and a quantity of isobutenes.

In practice, the oxygenate recycle stream 310, or at least a portion thereof, can be introduced directly into the oxygenate conversion zone 304 for further processing. Alternatively, the oxygenate recycle stream 310 may be combined with the oxygenate feedstock 302 and introduced into the oxygenate conversion zone 304 via the line 311.

At least a portion of the oxygenate conversion effluent stream 312 may be further processed in a separation or treatment zone 314 wherein the oxygenate conversion effluent stream 312 may be separated or fractionated such as by conventional distillation methods, to provide one or more process streams.

The oxygenate conversion effluent stream 312, or at least a portion thereof, is passed to a depropanizer zone 316. In the depropanizer zone 316, the oxygenate conversion effluent stream 312 is fractionated, such as by conventional distillation methods, such as to provide or form a depropanizer overhead stream 318 comprising $C_3$− hydrocarbons including methane, ethane, ethylene, propane, propylene and possibly also some inert species ($N_2$, CO, etc.), and a depropanized $C_4$+ bottoms stream 320 comprising components heavier than propane, such as mixed butenes and/or butane.

The depropanizer $C_3$− overhead stream 318, or at least a portion thereof, is passed to a deethanizer zone 322. In the deethanizer zone 322 the depropanizer $C_3$− overhead stream 318, or at least a portion thereof, is treated or fractionated, such as by conventional distillation methods, to provide or form a deethanizer overhead stream 324 comprising $C_2$− materials including ethylene and a deethanized stream 326 generally comprising $C_3$ materials including propane and propylene.

The deethanized stream 326, or at least a portion thereof, is passed to a $C_3$ splitter 328. In the $C_3$ splitter 328, the deethanized stream 326 is treated, e.g., fractionated, such as by conventional distillation methods, to provide an overhead propylene product stream 330 such as generally composed of propylene and a bottoms stream 332 such as generally composed of propane. The propane-containing bottoms stream 332, or a portion thereof, can be recycled to a front-end synthesis gas unit or, if such unit is not readily available, can be used as fuel.

The depropanized stream 320, or at least a portion thereof, is passed to a $C_4$ fractionation zone 334. In the $C_4$ fractionation zone 334, the depropanized stream 320 is fractionated, such as by conventional distillation methods, to provide or form a mixed butenes stream 336 generally composed of 1-butenes, 2-butenes and isobutenes, and a $C_4$+ stream 338 generally comprising $C_4$+ components other than butene.

In practice, the $C_4$+ stream 338, or a portion thereof, can be passed to a heavy hydrocarbon separation zone 340. In the heavy hydrocarbon separation zone 340, the $C_4$+ stream 338 is fractionated, such as by conventional distillation methods, to provide or form an overhead stream 342 generally composed of $C_5$ and/or $C_6$ hydrocarbons and a bottoms stream 344 generally comprising components heavier than hexane. In practice the overhead stream 342, or a portion thereof, can be recycled to the oxygenate conversion zone 304 for further processing. In practice, the bottoms stream 344 or a portion thereof can be used as fuel. For example, for locations in proximity to refineries, such materials or select portions thereof can be blended into a gasoline pool. Additionally or alternatively, depending upon the specifications as to the olefin content in a feed to a synthesis gas unit, the bottoms stream 344 or a portion thereof can be recycled to a front-end synthesis gas unit.

At least a portion of the mixed butenes stream 336 is passed to an isobutene conversion zone 346 wherein at least a portion of quantity of isobutenes from the mixed butenes stream 336 are converted to produce a second process stream 348 including a quantity of 1-butenes and a third process stream 350 including a conversion product. For example, the isobutenes from the mixed butenes stream 336 can be converted by reacting the isobutenes with methanol in the presence of an acid catalyst to produce the second process stream 348 and the third process stream 350 including a conversion product comprising methyl tert-butyl ether.

In accordance with certain embodiments, a portion of the oxygenate-containing feedstock 302 can be passed via a line 352 to the isobutene conversion zone 346 to react with at least a portion of the quantity isobutenes from the mixed butenes stream 336. At least a portion of the third process stream 350 can be recycled to oxygenate conversion zone 304 to produce an additional quantity of light olefins. For example, at least a portion of the third process stream 350 can be introduced directly into the oxygenate conversion zone 304. Alternatively, at least a portion of the third process stream 350 can be combined with the oxygenate-containing feedstock 302 and/or the overhead stream 342 and such combined stream can be introduced into the oxygenate conversion zone 304 via lines 376, 303, 305 and 311.

Alternatively, the isobutenes from the mixed isobutene stream 336 can be converted by dimerizing the isobutenes with 1-butene and/or 2-butene in the presence of an acid catalyst to produce the second process stream 348 and the third process stream 350 including a conversion product comprising $C_8$ and/or $C_{12}$ hydrocarbons. Such third process stream 350 can be introduced into the heavy hydrocarbon separation zone 340 wherein the $C_8$ and/or $C_{12}$ hydrocarbon components can be removed from the process 300 via the bottoms stream 344.

In accordance with one embodiment, the second process stream 348, or at least a portion thereof, can be passed to an isomerization zone 356 for isomerizing at least a portion of the quantity of 1-butenes from the second process stream 348 to form an isomerized stream 358 comprising an increased quantity of 2-butenes. The isomerization zone 356 may be configured and/or operated in a manner such as described above in conjunction with the isomerization zone 146, illustrated in FIG. 2.

At least a portion of the 2-butenes from the isomerized stream 358 and a quantity of ethylene, such as from an ethylene-containing process stream 364, are introduced into a metathesis zone 360 to produce a metathesis effluent stream 362 comprising propylene.

In accordance with certain embodiments, the deethanizer overhead stream 324 can be fractionated, such as by conventional distillation methods, to produce the ethylene-containing process stream 364. For example, the deethanizer overhead stream 324, or at least a portion thereof, can be passed to a demethanizer zone 366 wherein the overhead deethanizer stream 324 is fractionated to form a demethanizer overhead stream 368 comprising methane and possibly also some inert species ($N_2$, CO, etc.) and a demethanized stream 370 comprising $C_2$ materials including ethane and ethylene. At least a portion of the demethanized stream 370 is passed to a $C_2$ splitter 372 wherein the demethanized stream 370 is fractionated, such as by conventional distillation methods, to produce an ethane stream 374 and the ethylene-containing process stream 364. In accordance with certain embodiment, at least a portion of the demethanizer overhead stream 368 and/or the ethane stream 374 can be used as fuel.

The metathesis zone 360 can employ or contain a catalyst such as, for example, described above in conjunction with the metathesis zone 60, illustrated in FIG. 1. The metathesis of 2-butene with ethylene can, for example, be carried out in the vapor phase at about 300° C. to about 350° C. and about 0.5 MPa (75 psia) with a WHSV of 50 to 100 and a once-through conversion of about 15%, depending on the ethylene to 2-butene ratio. In accordance with certain embodiments, the metathesis zone 360 can include a reaction with distillation column as described above in conjunction with metathesis zone 154, illustrated in FIG. 2.

Propylene is desirably recovered from the metathesis effluent stream 362. In accordance with one embodiment, at least a portion of the metathesis effluent stream 362 can be recycled into the separation or treatment zone 314. For example, at least a portion of the metathesis effluent stream 362 can be combined with at least a portion of the oxygenate conversion effluent stream 312 and such combined stream can be introduced via a line 380 into the separation zone 314 wherein propylene can be recovered from such combined stream according to the process described above in conjunction with the depropanizer zone 316, the deethanizer zone 322 and the $C_3$ splitter 328.

Figure 5:
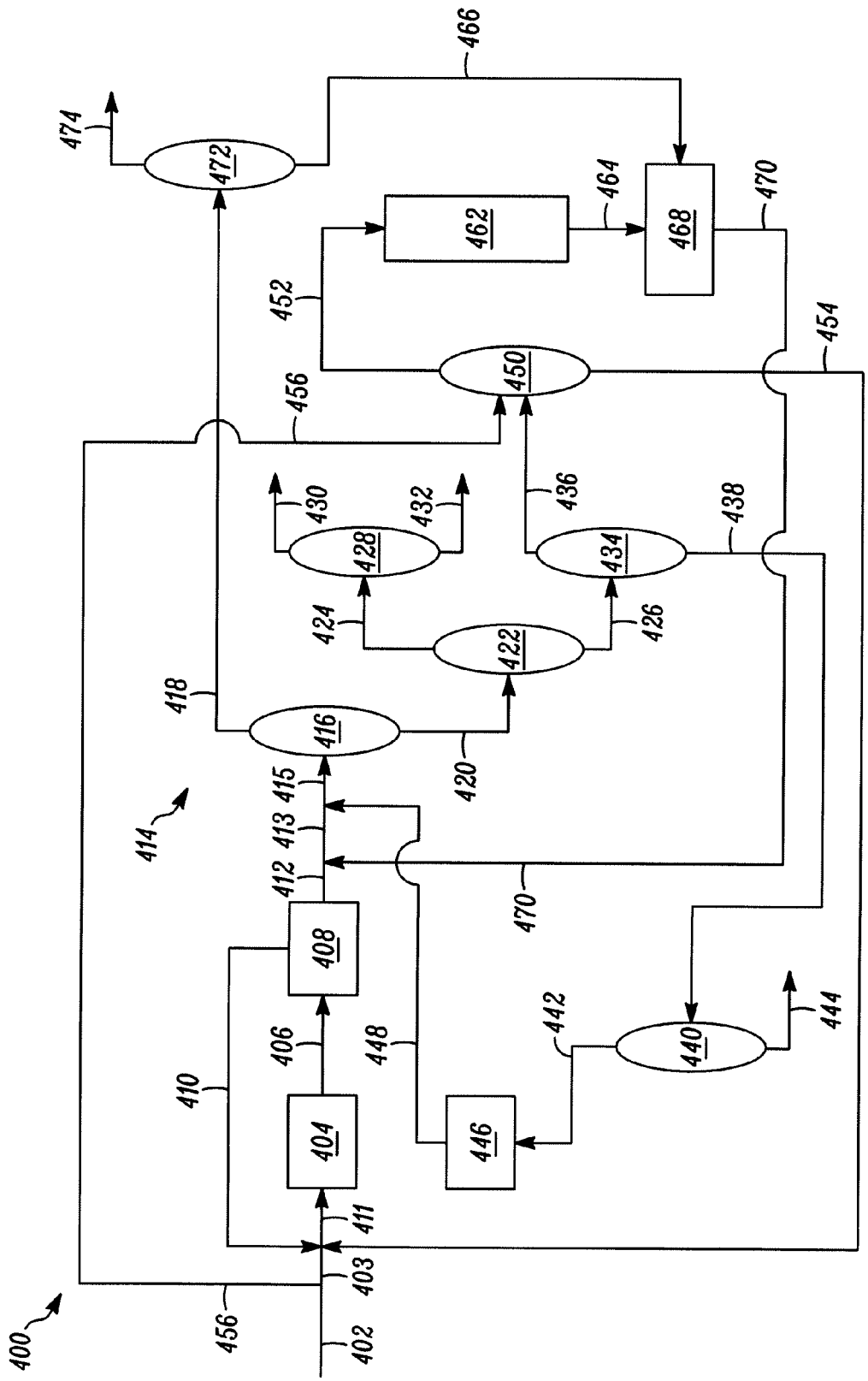
FIG. 5 is a simplified schematic process flow diagram illustrating a process for the conversion of oxygenates to olefins and employing first and second oxygenate conversion zones, to enhance the relative yield of propylene, a separation zone, to form a butene-containing stream, an isobutene conversion zone, to reduce the relative amount of isobutenes, an isomerization zone, to enhance the relative amount of 2-butene, and a metathesis zone, to enhance the yield of propylene, in accordance with another embodiment.

In accordance with another embodiment, as illustrated in FIG. 5, a processing scheme 400 for producing light olefins from an oxygenate-containing feedstock involves introducing an oxygenate-containing feedstock or feedstream 402 is introduced via lines 403 and 411 into an oxygenate conversion zone 404 wherein the oxygenate-containing feedstock contacts an oxygenate conversion catalyst at reaction conditions effective to convert the oxygenate-containing feedstock to form an oxygenate conversion reactor effluent stream 406 comprising fuel gas hydrocarbons, light olefins, and $C_4+$ hydrocarbons.

In accordance with certain embodiments, the oxygenate conversion zone 404 includes at least one oxygenate conversion reactor such as, for example, a moving bed reactor containing particles of a molecular sieve-based dual-function catalyst material. Such catalyst material can comprise a zeolitic molecular sieve having a structure corresponding to ZSM-5 or ZSM-11 or contain an ELAPO molecular sieve having a structure corresponding to SAPO-34 or a combination thereof. The oxygenate conversion reactor can be operated at an inlet temperature in a range of about 350° C. to about 500° C., preferably in a range of 375° C. to 500° C., or in a range of 375° C. to 475° C. The oxygenate conversion reactor can be operated at an inlet pressure of about 101.3 kPa to 304 kPa (about 1 atm to 3 atm), preferably about 136 kPa to 343 kPa (5 psig to 35 psig). The WHSV for the oxygenate conversion reactor can range from about 0.1 $hr^{-1}$ to 100 $hr^{-1}$, preferably from about 0.5 $hr^{-1}$ to 20 $hr^{-1}$, or from about 0.5 $hr^{-1}$ to 10 $hr^{-1}$.

The oxygenate conversion reactor effluent stream 406, or at least a portion thereof, is treated in an oxygenate recovery zone 408 to produce or result in the formation of an oxygenate recycle stream 410 and an oxygenate conversion effluent stream 412 which comprises a quantity of light olefins including ethylene and a quantity of $C_4+$ hydrocarbons including a quantity of butenes such as including a quantity of 1-butenes, a quantity of 2-butenes and a quantity of isobutenes. In practice, the oxygenate recycle stream 410 can be combined with the oxygenate feedstock 402 and introduced into the oxygenate conversion zone 404 via the line 411.

The oxygenate conversion effluent stream 412, or at least a portion thereof, is passed to a separation zone 414. In practice, the oxygenate conversion effluent stream 412 is introduced into a deethanizer zone 416 via lines 413 and 415 and is fractionated, such as by conventional distillation methods, to provide or form a deethanizer overhead stream 418 comprising $C_2-$ hydrocarbons including methane, ethane, ethylene, and possibly also some inert species ($N_2$, CO, etc.), and a deethanized $C_3+$ bottoms stream 420 comprising components heavier than ethane, such as propylene, propane, mixed butenes and/or butane.

The deethanized $C_3+$ bottoms stream 420, or at least a portion thereof, is passed to a depropanizer zone 422 wherein the deethanized $C_3+$ bottoms stream 420 is treated or fractionated to form a depropanizer overhead stream 424 comprising $C_3$ materials and a depropanized stream 426 generally comprising $C_4+$ components. The depropanizer overhead stream 424, or at least a portion thereof, is passed to a $C_3$ splitter 428 wherein the depropanizer overhead stream 424 is treated, e.g., fractionated, to provide an overhead propylene product stream 430 such as generally composed of propylene and a bottoms stream 432 such as generally composed of propane.

The depropanized stream 426, or at least a portion thereof, is passed to a $C_4$ fractionation zone 434 wherein the depropanized stream 426 is fractionated, such as by conventional distillation methods, to form a mixed butenes stream 436 generally composed of 1-butenes, 2-butenes and isobutenes, and a $C_4+$ stream 438 generally comprising $C_4+$ components other than butene.

In practice, the $C_4+$ stream 438, or at least a portion thereof, can be passed to a heavy hydrocarbon separation zone 440 wherein the $C_4+$ stream 438 is fractionated, such as by conventional distillation methods, to provide or form an overhead stream 442 generally composed of $C_5$ and/or $C_6$ hydrocarbons and a bottoms stream 444 generally comprising components heavier than hexane.

The overhead stream 442, or a portion thereof, can be passed to a heavy olefin interconversion zone 446 to produce a heavy olefin interconversion effluent stream 448 comprising propylene. In accordance with certain embodiments, the heavy olefin interconversion zone 446 includes at least one heavy olefin interconversion reactor including a moving bed reactor containing particles of a molecular sieve-based dual-function catalyst and operated at heavy olefin interconversion conditions to produce an additional quantity of propylene. In practice, the catalyst material employed in the heavy olefin interconversion zone 446 comprises the same catalyst material employed in the oxygenate conversion zone 404. For example, such catalyst material may contain a zeolitic molecular sieve having a structure corresponding to ZSM-5 or ZSM-11 or contain an ELAPO molecular sieve having a structure corresponding to SAPO-34 or a combination of these materials.

The heavy olefin conversion reactor can be operated at an inlet temperature at least about 15° C. to 25° C., or more, higher than the maximum temperature employed in the oxygenated conversion zone 404. The heavy olefin interconversion reactor can be operated at an inlet pressure of about 101.3 kPa to 304 kPa (about 1 atm to 3 atm), preferably about 136 kPa to 343 kPa (5 psig to 35 psig). The WHSV for the heavy olefin interconversion reactor can range from about 0.1 $hr^{-1}$ to 100 $hr^{-1}$, preferably from about 0.5 $hr^{-1}$ to 20 $hr^{-1}$, or from about 0.5 $hr^{-1}$ to 10 $hr^{-1}$.

The heavy olefin interconversion effluent stream 448, or at least a portion thereof, can be introduced into the separation zone 414 such as via the line 415 wherein the heavy olefin interconversion effluent stream 448 can be treated, e.g., fractionated, such as described in detail above in conjunction with the deethanizer zone 416, the depropanizer zone 422, the $C_3$ splitter 428, and the $C_4$ fractionation zone 434.

At least a portion of the mixed butenes stream 436 is passed to an isobutene conversion zone 450 wherein at least a portion of quantity of isobutenes from the mixed butenes stream 436 are converted, such as by reacting the isobutenes with an oxygenate-containing material such as, for example, methanol, ethanol or a combination thereof, to produce a second process stream 452 including a quantity of 1-butenes and a third process stream 454 including a tertiary ether or alcohol product. A portion of the oxygenate-containing feedstock 402 can be passed via a line 456 to the isobutene conversion 450 to react with at least a portion of the quantity isobutenes from the mixed butenes stream 436. At least a portion of the third process stream 454 can be combined with the oxygenate-containing feedstock 402 and introduced into the oxygenate conversion zone 404 via the line 411.

The second process stream 452, or at least a portion thereof, can be passed to an isomerization zone 462 for isomerizing at least a portion of the quantity of 1-butenes from the second process stream 452 to form an isomerized stream 464 comprising an increased quantity of 2-butenes. The isomerization zone 462 may be configured and/or operated in a manner such as described above in conjunction with the isomerization zone 146, illustrated in FIG. 2.

In accordance with certain embodiments, the deethanizer overhead stream 418 can be fractionated, such as by conventional distillation methods, in a demethanizer zone 472 to produce a demethanizer overhead stream 474 comprising methane and possibly also some inert species ($N_2$, CO, etc.) and a demethanized stream 466 comprising $C_2$ materials including ethylene and ethane. At least a portion of the 2-butenes from the isomerized stream 464 and a quantity of ethylene from the demethanized stream 466 are introduced into a metathesis zone 468 to produce a metathesis effluent stream 470 comprising propylene.

The metathesis zone 468 can employ or contain a catalyst such as, for example, described above in conjunction with the metathesis zone 60, illustrated in FIG. 1. The metathesis of 2-butene with ethylene can, for example, be carried out in the vapor phase at about 300° C. to about 350° C. and about 0.5 MPa (75 psia) with a WHSV of 50 to 100 and a once-through conversion of about 15%, depending on the ethylene to 2-butene ratio.

At least a portion of the metathesis effluent stream 470 can be recycled into the separation or treatment zone 414. For example, at least a portion of the metathesis effluent stream 470 can be combined with at least a portion of the oxygenate conversion effluent stream 412 and such combined stream can be introduced into the separation zone 414 via lines 413 and 415 wherein propylene can be recovered from such combined stream according to the process described above in conjunction with the depropanizer zone 416, the deethanizer zone 422 and the $C_3$ splitter 428.

Thus, through the application of 1-butene/2-butene cross-metathesis, butene isomerization, isobutene conversion or removal, and/or 2-butene/ethylene metathesis, such as described above, there are provided processes and systems for the conversion of an oxygenate-containing feedstock to olefins that maximizes the production to a greater extent than heretofore practically realized. Moreover, processing schemes and arrangements are provided that are desirably effective and efficient in increasing the relative yield of propylene in association with oxygenated conversion of light olefins. In particular, the processing and system integration of the conversion of oxygenated to olefins with metathesis, isobutene conversion and/or isomerization, as described herein, can desirably result in achieving propylene to ethylene product ratios of at least two or more.

The invention illustratively disclosed herein suitably may be practiced in the absence of any element, part, step, component, or ingredient which is not specifically disclosed herein.

While in the foregoing detailed description this invention has been described in relation to certain embodiments thereof, and many details have been set forth for the purpose of illustration, it will be apparent to those skilled in the art that the invention is susceptible to additional embodiments and that certain of the details described herein can be varied considerably without departing from the basic principles of the invention.

The invention claimed is:

1. A process for producing light olefins from an oxygenate-containing feedstock including at least a quantity of methanol, the process comprising:

contacting the oxygenate-containing feedstock in an oxygenate conversion reactor with an oxygenate conversion catalyst and at reaction conditions effective to convert the oxygenate-containing feedstock to an oxygenate conversion effluent stream comprising light olefins and C4+ hydrocarbons, wherein the light olefins comprise ethylene and the C4+ hydrocarbons comprise a quantity of butenes including a quantity of 1-butenes and a quantity of isobutene;

treating the oxygenate conversion effluent stream and forming a first process stream comprising at least a portion of the butenes including a quantity of isobutenes and a quantity of 1-butenes from the oxygenate conversion effluent stream;

converting at least a portion of quantity of isobutenes from the first process stream in an isobutene conversion zone to form a second process stream including a quantity of 1-butenes and a third process stream including a conversion product;

isomerizing at least a portion of the 1-butenes from the second process stream in an isomerization zone to form an isomerized stream comprising a quantity of 2-butenes;

contacting at least a portion of the quantity of 2-butenes from the isomerized stream with ethylene in a metathesis zone comprising a reaction distillation column containing a fixed bed of the metathesis catalyst and wherein upon contact with the metathesis catalyst at least a portion of the quantity of 2-butenes from the isomerized stream is metathesized with ethylene in the fixed bed to produce the metathesis effluent stream comprising propylene and a metathesis bottoms stream;

recycling at least a portion of the metathesis bottoms stream to the oxygenate conversion zone; and recovering propylene from the metathesis effluent stream.

2. The process of claim 1 wherein the treating step additionally forms a fourth process stream comprising at least a portion of the ethylene from the oxygenate conversion effluent stream and wherein at least a portion of the ethylene from the fourth process stream is introduced into the metathesis zone to metathesize at least a portion of the quantity of 2-butenes to produce propylene.

3. The process of claim 1 wherein the converting step comprises introducing a portion of the oxygenate-containing feedstock into the isobutene conversion zone wherein during an isobutene conversion reaction at least a portion of the quantity of isobutenes is converted to produce a conversion product comprising methyl tert-butyl ether.

4. The process of claim 1, wherein the converting step comprises dimerizing at least of the portion of isobutenes from the first process stream in the isobutene conversion zone to produce the conversion product.

5. The process of claim 1 wherein the $C_4+$ hydrocarbons from the oxygenate conversion effluent stream additionally comprise a quantity of 2-butenes and wherein during the metathesis step, at least a portion of the quantity of 2-butenes is also metathesized with ethylene in the metathesis zone to produce additional propylene included in the metathesis effluent stream.

6. The process of claim 1 wherein the metathesis effluent stream additionally comprises a quantity of butenes, the process further comprising:

separating at least a portion of the quantity of butenes from the metathesis effluent stream; and recycling at least a portion of the separated butenes to the isobutene conversion zone.

* * * * *